(12) United States Patent
Arkinstall

(10) Patent No.: US 7,001,367 B2
(45) Date of Patent: Feb. 21, 2006

(54) VALVED OSTOMY DRAINAGE DEVICE

(76) Inventor: William W. Arkinstall, #4-757 KLO Road, Kelowna, British Columbia (CA) V1Y 9L8

( * ) Notice: Subject to any disclaimer, the term of this patent is extended or adjusted under 35 U.S.C. 154(b) by 311 days.

(21) Appl. No.: 10/249,511

(22) Filed: Apr. 15, 2003

(65) Prior Publication Data

US 2003/0220621 A1 Nov. 27, 2003

Related U.S. Application Data

(60) Provisional application No. 60/372,430, filed on Apr. 16, 2002.

(51) Int. Cl.
*A61F 5/44* (2006.01)
(52) U.S. Cl. .................................. 604/337
(58) Field of Classification Search ................ 604/332, 604/334, 337, 335
See application file for complete search history.

(56) References Cited

U.S. PATENT DOCUMENTS

| | | | |
|---|---|---|---|
| 2,542,233 A * | 2/1951 | Carroll ..................... 604/337 |
| 4,241,735 A | 12/1980 | Chernov |
| 4,344,434 A | 8/1982 | Robertson |
| 4,351,322 A | 9/1982 | Prager |
| 4,381,765 A | 5/1983 | Burton |
| 4,634,421 A | 1/1987 | Hegemann |
| 4,642,107 A | 2/1987 | Arnone et al. |
| 4,721,508 A | 1/1988 | Burton |
| 5,045,052 A * | 9/1991 | Sans ........................... 600/32 |
| 5,098,420 A | 3/1992 | Iacone |
| 5,269,774 A | 12/1993 | Gray |
| 5,287,852 A | 2/1994 | Arkinstall |
| 5,342,321 A * | 8/1994 | Potter ........................ 604/174 |
| 5,501,677 A | 3/1996 | Jensen |
| 5,569,216 A | 10/1996 | Kim et al. |
| 5,865,820 A * | 2/1999 | Myello et al. ............. 604/345 |

FOREIGN PATENT DOCUMENTS

| | | |
|---|---|---|
| CA | 1170139 | 7/1984 |
| CA | 1174001 | 9/1984 |
| CA | 1233086 | 2/1988 |
| CA | 1239559 | 7/1988 |
| CA | 1243915 | 11/1988 |
| CA | 1278484 | 1/1991 |
| CA | 2150397 | 5/1995 |
| CA | 2208552 | 7/1996 |

* cited by examiner

*Primary Examiner*—Sharon Kennedy
(74) *Attorney, Agent, or Firm*—Antony C. Edwards

(57) ABSTRACT

The valved ostomy drainage device of the present invention includes a primary conduit which may be inserted into either a colonoscopy or ileostomy. Once inserted, a balloon cuff or collar on the inner aspect of the conduit is inflated which holds the conduit in place in the ostomy. The conduit is anchored on the exterior surface of the patient by a soft, malleable ring which acts as a resilient pad seal and by an anchoring collar which mounts onto the exposed end of the conduit to sandwich the ring against the patient's abdomen. With the collar so mounted the remaining exposed end of the conduit is adapted for sealing by the releasable mounting thereon of a rigid sealing member such as a threaded cap or other means of closure. A flexible one-way valve mounted in the conduit inhibits waste such as bowel contents or stool extruding through the conduit until the cap is removed and the one-way valve biased open by a secondary conduit inserted into the primary conduit and pushed against the one-way valve so as to open the valve.

16 Claims, 4 Drawing Sheets

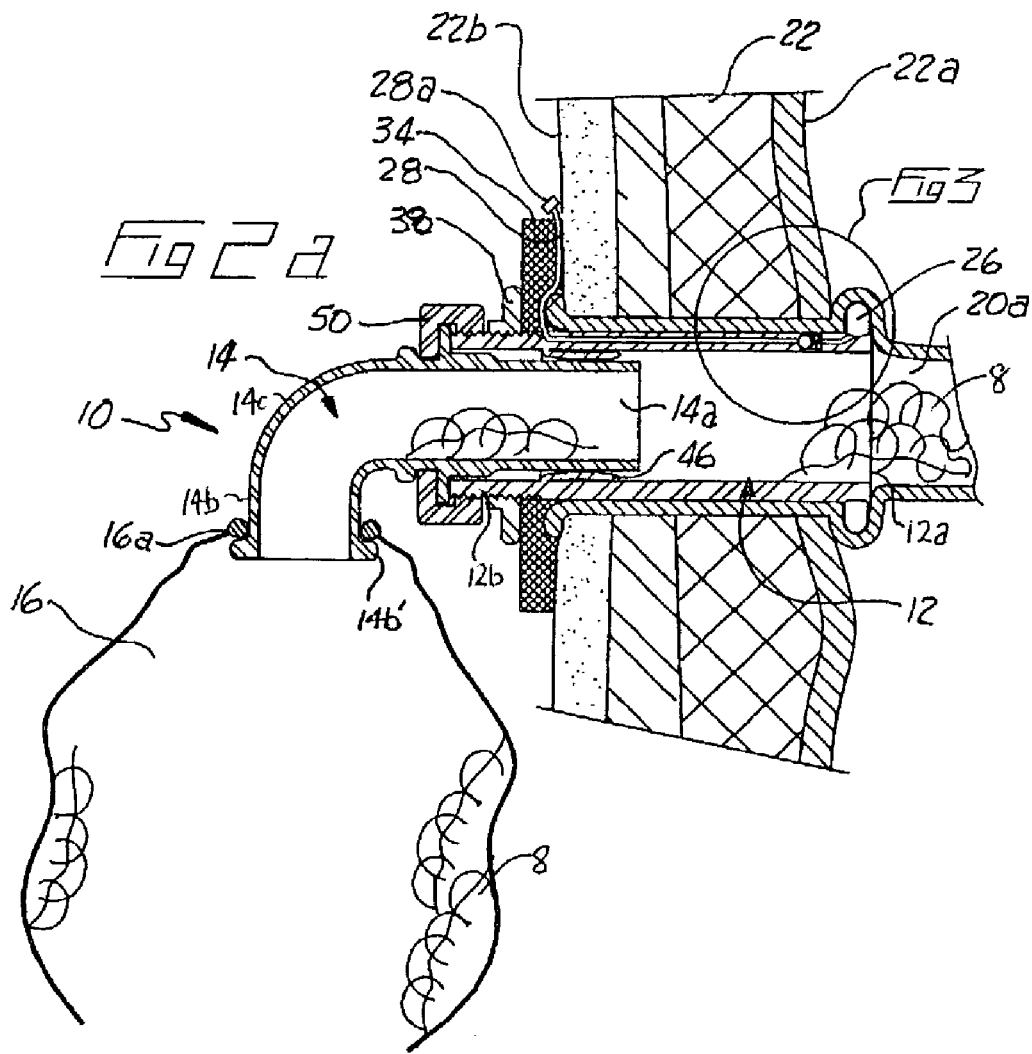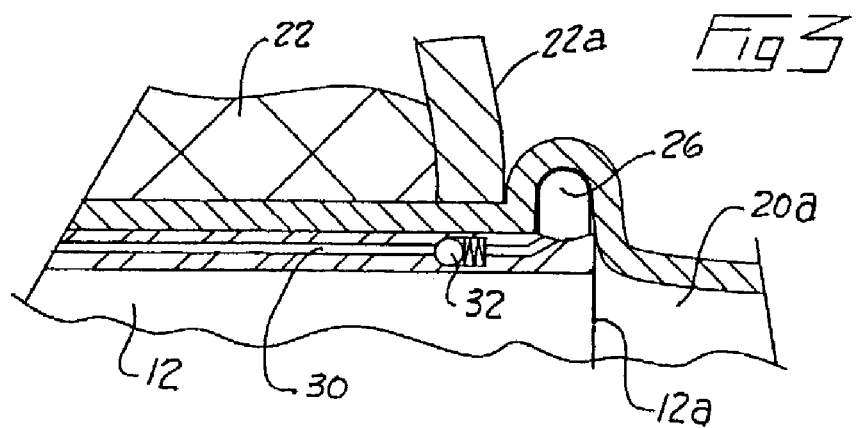

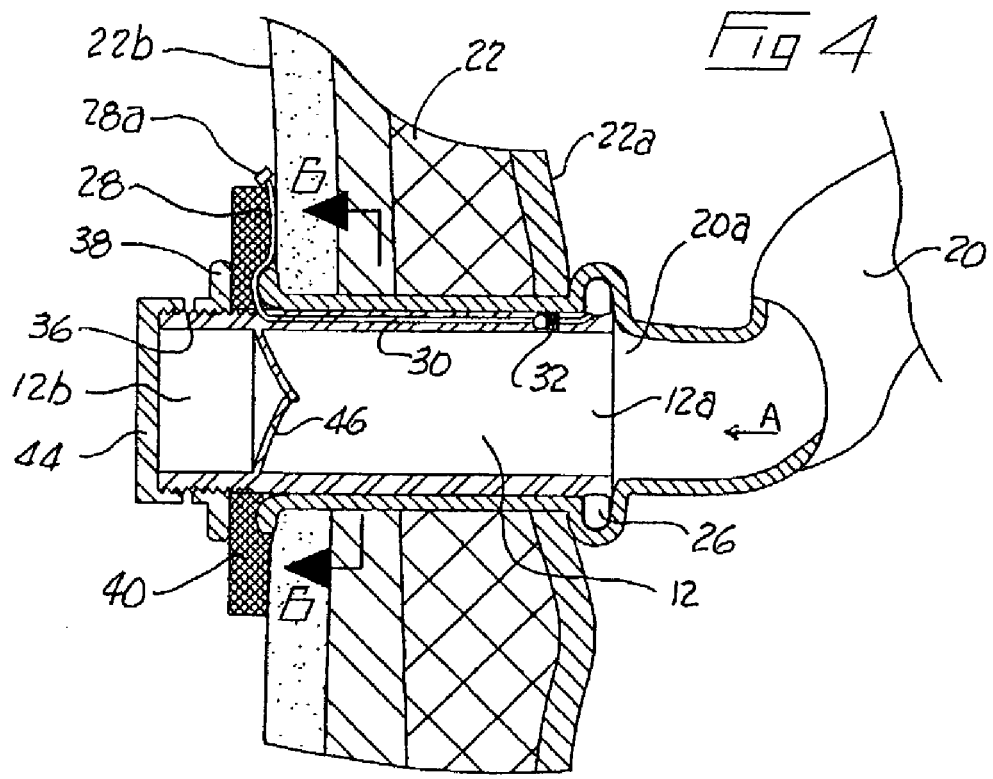
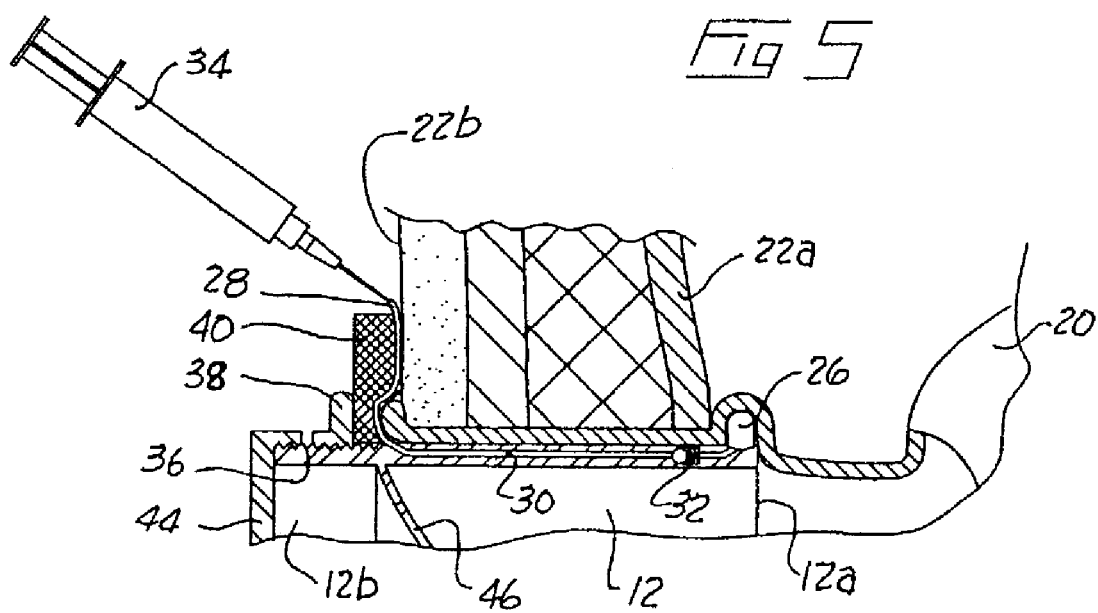

VALVED OSTOMY DRAINAGE DEVICE

CROSS REFERENCE TO RELATED APPLICATIONS

This application claims priority from U.S. Provisional Patent Application No. 60/372,430 filed Apr. 16, 2002 entitled Valved Ostomy Drainage Device.

BACKGROUND OF INVENTION

This invention relates to the field of ostomy drainage devices.

Patients frequently have bowel diseases, most often cancer, which requires removing the lower portion of the bowel, therefore interrupting the normal flow on the intestinal contents and normal evacuations via the rectum. These patients have either their large bowel, the colon, introduced through anterior abdominal wall as a colonoscopy; or, the small intestine, the ileum, brought through the anterior abdominal wall as an ileostomy. That is, a large bowel or small intestine resection may necessitate a surgically created ostomy through a portion of the abdominal wall for the evacuation of bodily waste. In such cases the proximal portion of the severed bowel is drawn through the abdominal wall and secured to the exterior surface of the abdomen. A waste receptacle is generally required to be continuously held or mounted in place over the stoma and removed for emptying. Such receptacles are generally not readily disposable in the standard sewer or septic system and are not reusable.

Conventionally such individuals wear a bag attached to the anterior abdominal surface which continually collects stool and bowel contents throughout a twenty four hour period. Patients empty the bag periodically and replace it with a new collection apparatus. Therefore, such individuals are always walking around with a collection bag with various amounts of bowel contents. Even though these devices are worn under a patient's clothes, the patient remains aware of the presence of the device and the collection bag. Such collection bags when worn continuously, will, as one may envision, greatly restrict the normal activities of the wearer such as swimming, bathing, may be prone to leakage and to the emitting of unwanted odours.

In the prior art applicant is aware of U.S. Pat. No. 4,344,434 which issued to Robertson on Aug. 17, 1982 for an ileostomy Appliance and Method for Implementing the Same. Robertson discloses the use of a tube which is inserted into an ostomy so as to abut a plate at one end of the tube against the patient's skin. An inflatable balloon at the other end of the tube is employed to anchor the tube in the ostomy. A flexible unidirectional valve, taught to be a miter valve, is mounted within the tube. The unidirectional valve has flexible sealing members the ends of which are located remotely from the plate. The ends of the flexible sealing members terminate in flexible lips which are normally biased to maintain the edges thereof in engagement with each other to form a fluid-tight seal. A catheter is provided which when inserted through the plate end of the tube engages the flexible sealing members of the unidirectional valve so as to separate the edges of the flexible lips to form an opening through which the catheter may be inserted. The edges of the flexible lips form a fluid-tight sliding sealing engagement with the exterior outer surface of the catheter.

The catheter of Robertson has a conically shaped stop which prevents further sliding of the catheter into the tube once the catheter has been pushed through the unidirectional valve. The opposite end of the catheter may be angled relative to the end inserted into the tube and may be adapted to have a drain tube removably attached thereto for fluid communication into a fluid collecting member. What is not provided for, and which is an object of the present invention to provide, is a further means of sealing unwanted discharge from the ostomy in the event that the unidirectional valve leaks, for example due to diminished resilient biasing of the sealing members caused by hysteresis of the valve material, or, when the valve is in the opened position, due to a faulty seal around the circumference of the catheter. Thus a backup sealing device is provided for continent sealing of the ostomy drainage device when the patient does not desire to wear an ostomy collection bag and for sealing around the ostomy during discharge of waste into an ostomy collection bag.

It is, therefore, another object of the present invention to mount securely within a bowel ostomy a valved drainage conduit that is securely sealable by a threaded cap or other means of closure against leakage of either liquid or vapor.

SUMMARY OF INVENTION

The valved ostomy drainage device of the present invention includes a primary conduit which may be inserted into either a colonoscopy or ileostomy. Once inserted, a balloon cuff or collar on the inner aspect of the conduit is inflated which holds the conduit in place in the ostomy. The conduit is anchored on the exterior surface of the patient by a soft, malleable ring which acts as a resilient pad seal and by an anchoring collar which mounts onto the exposed end of the conduit to sandwich the ring against the patient's abdomen. With the collar so mounted the remaining exposed end of the conduit is adapted for sealing by the releasable mounting thereon of a rigid sealing member such as a threaded cap or other means of closure. A flexible one-way valve mounted in the conduit inhibits waste such as bowel contents or stool extruding through the conduit until the cap is removed and the one-way valve biased open by a secondary conduit inserted into the primary conduit and pushed against the one-way valve so as to open the valve.

The secondary conduit may be secured onto the end of the primary conduit by a threaded collar or other means of attachment substituted for the cap. A collection bag is attached onto the exposed end of the secondary conduit.

Thus the present invention may be described as a sealable, valved conduit mountable within an ostomy. The conduit has an annular inflatable cuff inside the body, at its upstream end, which when collapsed facilitates ready insertion through the ostomy to a position adjacent to the inner surface of the anterior surface of the abdominal wall. The annular cuff is inflated by means of a passageway formed integrally with the wall of the drainage conduit. A one-way valve within the passageway prevents deflation of the cuff. In its inflated aspect, the cuff expands and distends the bowel wall slightly annularly outwardly, to prevent accidental removal of the conduit. A collar threaded over the threaded downstream end of the conduit secures it in place. A soft, resilient, pressure-absorbing distendable and collapsible pad sandwiched between the collar and the abdomen may be used to protect the stoma and adjacent abdomen against the buildup of any pressure in the intestinal mucosa or against the inner abdominal wall.

A tricuspid or other one-way valve for example of the kind having flaps of tent-like arrays of resilient or flexible members, leaflets, petals or vanes which are resiliently biased to a normally closed position is mounted within the ostomy conduit. Pressure against the face of the valve from waste, whether solid, liquid or gas exiting the bowel exerts pressure against the normally closed valve thus preventing or at least inhibiting leakage.

The downstream end of the ostomy drainage conduit projects a short distance outwardly from the anterior abdominal wall of the patient. The downstream end is threaded or shaped to accept a cap or other means of closure which secures the downstream end, providing a back-up seal which further and finally demountably seals the ostomy drainage conduit against leakage of waste solids, liquid or vapors.

A separate evacuation tube, which may be formed as a ninety degree or otherwise L-shaped elbow, has an upstream end adapted to pass inwardly from the downstream end of the ostomy drainage conduit and a downstream end adapted to retain a removable waste drainage receptacle such as an ostomy bag. The use of the evacuation tube and waste drainage receptacle need only be used at such times as the wearer finds convenient to evacuate the bowel. Secure connection of the evacuation tube with the drainage conduit is accomplished by means of a rotatable collar or other means to attach on the evacuation tube, onto the projecting downstream end of the drainage conduit.

Inserting the evacuation tube within drainage tube brings its upstream end into contact with the anterior face of the valve. As the evacuation tube is further inserted and the collar on the evacuation tube is tightened on to the ostomy drainage conduit, the valve is forced open permitting bowel contents to pass through the evacuation tube and into the attached waste receptacle for disposal. The waste receptacle may be manufactured from readily degradable material which may be flushed down a toilet.

Brief_Description_of_the_DrawingsBrief_Description_of_the_DrawingsIn summary, the valved ostomy drainage device of the present invention includes a hollow first and second conduit. The first conduit has first and second opposite ends. The first end has an inflatable toroidal or annular anchor (hereinafter collectively referred to as an annular anchor) mounted thereto for selective inflation so as to anchor the first end with a patient's bowel ostomy behind the abdominal wall of the patient. The second end may be cylindrical and externally threaded. The first conduit is of sufficient length so that, with the anchor inflated and snug against the interior surface of the abdominal wall, a portion of the second end protrudes from the stoma.

A threaded first collar is mountable onto the second end of the first conduit so that, once snugged against the exterior surface of the abdomen, or against a resilient pad sandwiched between the first collar and the patient's abdomen, the inflated anchor is held snugly against the abdominal wall. With the first collar so mounted, a length of the second end of the first conduit is left protruding from the first collar for mounting thereon of a screw-on cap or other means to provide a removable and re-usable fluid and gas seal on the second end of the first conduit.

The cap or similar closing mechanism provides a backup seal to a one-way valve mounted in the first conduit. The one-way valve is normally resiliently biased closed to inhibit fluid flow from the first end to the second end of the first conduit. The one-way valve is adapted to be pushed open by the insertion of the second conduit in a sliding telescoping fit into the first conduit, so as to journal a first end of the second conduit through the one-way valve into fluid communication with the first end of the first conduit.

A threaded second collar or other method of attachment is mounted on the second conduit, so that, with the cap removed and the second conduit inserted into the first conduit and through the one-way valve, the second collar may be threadably mated or otherwise connected onto the protruding portion of the second end protruding from the first collar. The second collar and its rotatable mating onto the second conduit are adapted to seal the sliding fitment of the second conduit into the first conduit when the second collar is snugly mated onto the second end of the first conduit or other mechanism.

BRIEF DESCRIPTION OF DRAWINGS

FIG. 2a is a sectional view taken on line 2a—2a of FIG. 2.

FIG. 3 is an enlarged sectional view of a portion of FIG. 2a.

FIG. 4 is a sectional view through the drainage conduit in its closed aspect.

FIG. 5 is an enlarged sectional view illustrating the annular cuff inflating procedure.

DETAILED DESCRIPTION

Figure 1:
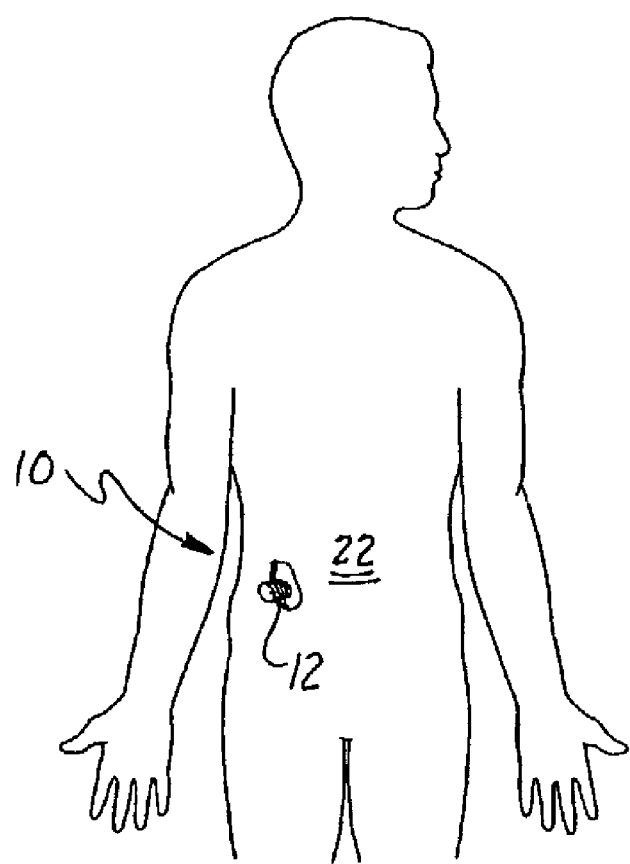
FIG. 1, is a frontal view of a human figure with the valved drainage conduit securely closed by a threaded cap.
Figure 2:
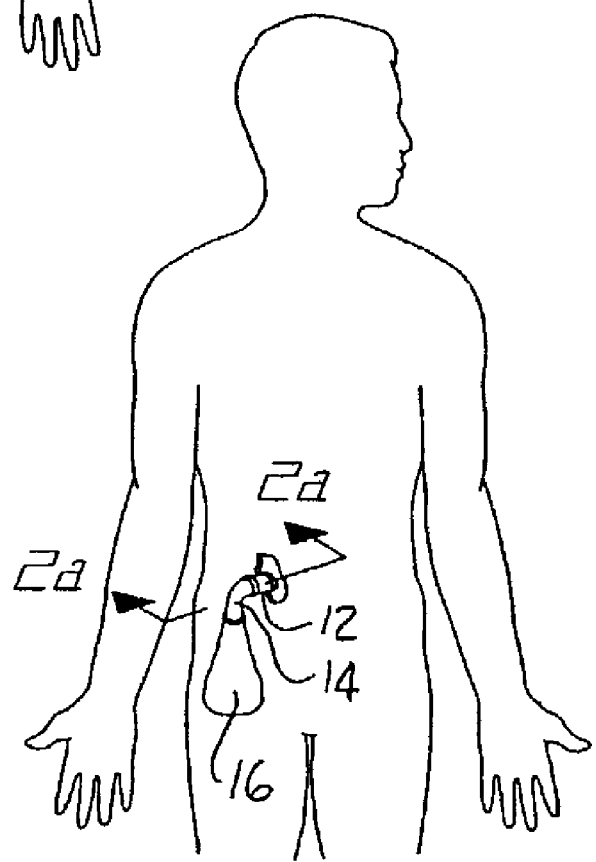
FIG. 2 is a frontal view of a human figure with the evacuation tube and waste drainage receptacle secured to the valved drainage conduit.
Figure 6:
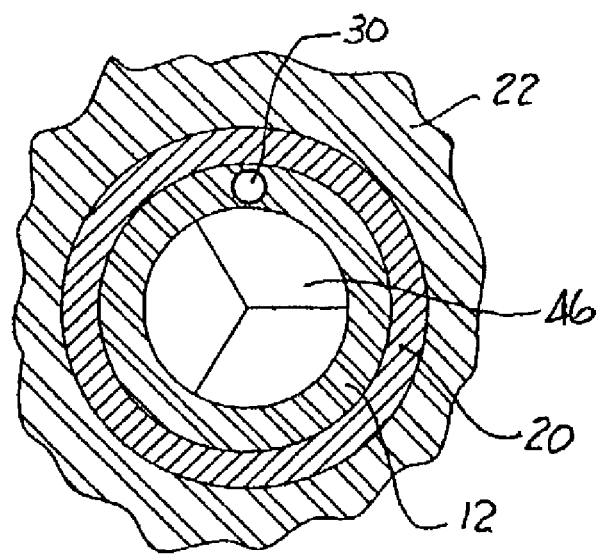
FIG. 6 is a sectional view taken on line 6—6 of FIG. 4.
Figure 7:
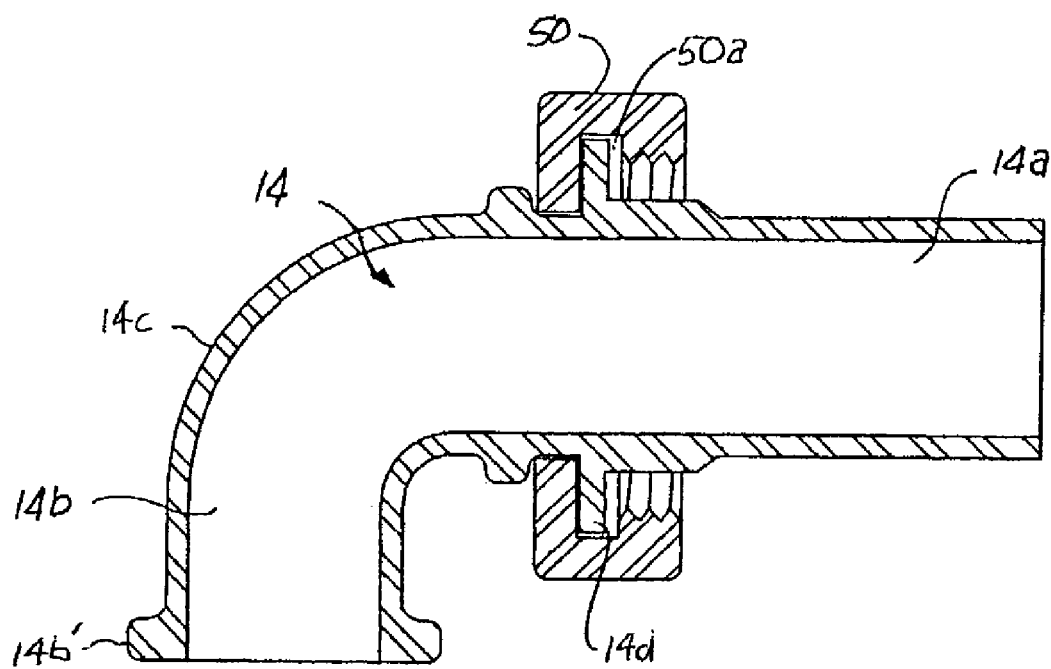
FIG. 7 is a sectional view through the evacuation tube.

With reference to the drawing figures, wherein similar characters of reference denote corresponding parts in each view, the ostomy drainage device 10 of the present invention includes a valved drainage conduit 12 and a separate evacuation tube 14, having attached thereto a readily disposable waste receptacle 16.

Conduit 12 has opposite first and second ends, alternatively referred to herein as upstream and downstream ends 12a and 12b respectively. Conduit 12 is rigid or slightly resilient and is mounted within a surgically created ostomy at the downstream portion 20a of a severed bowel as a colonoscopy or ileostomy 20. Upstream end 12a of drainage conduit 12 is positioned adjacent to the anterior surface 22a of an abdominal wall 22 while downstream end 12b is left extending from the ostomy so as to project a short distance outwardly of the posterior surface 22b of abdominal wall 22.

An inflatable annular cuff 26 is integrally formed around the circumference of conduit 12 at upstream end 12a. Cuff 26 is inflated by air injected into an exterior air conduit such as inflation tube 28, passageway 30 formed within the wall of conduit 12 connecting tube 28 to cuff 26. A closure cap 28a is provided to seal closed the free end of tube 28. A one-way check valve such as ball valve 32 in passageway 30 prevents reverse airflow from cuff 26 so as to maintain air pressure in the cuff once inflated. Cuff 26 may be inflated using for example a syringe 34 as illustrated, or by other suitable air pressurizing means. Upon inflation, cuff 26 slightly distends the adjacent annular portion of bowel 20 to securely retain the cuff and the corresponding portion of bowel behind anterior surface 22a and releasably inhibit conduit 12 from dislodging and translocating to the exterior of the abdominal wall.

External helical threads 36 are formed on the downstream end 12b of drainage conduit 12. Collar 38 is threaded onto threads 36 until it is snug against a pressure-absorbing pad 40 journalled onto downstream end 12b and sandwiched between collar 38 and surface 22b of abdominal wall 22. This inhibits dislodging and translation of conduit 12 to the anterior of abdominal wall 22. Pad 40 further inhibits abrasion of both exterior abdominal surface 22b and inflation tube 28 by collar 38. A threaded cap 44 is provided for threading onto downstream end 12b of drainage conduit 12 to selectively close off and seal end 12b.

Valve 46 is formed internally in downstream end 12b of conduit 12. Valve 46 is a one-way flap valve. It opens in a direction toward upstream end 12a conduit 12 so that pressure from liquid or gasses passing through the bowel in direction A, toward downstream end 12b, urge valve 34 into its normally closed position thereby preventing the build-up of waste against the inside of cap 44 and accidental leakage. The use of cap 44 to close-off downstream end 12b permits the patient to select the most convenient time for bowel evacuation into waste receptacle 16, so that an external waste drainage receptacle does not have to be continuously attached to the patient as in the prior art.

Evacuation tube 14 may in one embodiment, not intended to be limiting, be formed as a right-angled rigid elbow. A first or upstream end 14a of tube 14, has an exterior diameter which permits it to snugly slide inwardly into downstream end 12b of drainage conduit 12. An internally threaded collar 50 is mounted on to tube 14 upstream of elbow 14c. The opposite second or downstream end 14b of evacuation tube 14 is formed downstream of elbow 14c generally at right-angles to end 14a. End 14b is adapted to removably retain thereon a disposable waste receptacle 16. For example, in the illustrated embodiment, end 14b of tube 14 has a raised annular lip 14b' for retaining on end 14b a resilient ring or neck 16a of waste receptacle 16, where receptacle 16 may be a flexible non-porous bag for retaining therein waste 8.

Evacuation tube 14 is releasably mounted onto end 12b of drainage conduit 12 by threading collar 50 onto the exterior threads of end 12b. Collar 50 is rotatably mounted onto tube 14 by a rotatable mating or coupling of annular groove 50a within collar 50 onto annular ring or flange 14d extending from tube 14. Insertion of end 14a of tube 14 into end 12b of conduit 12 brings first end 14a into contact with flap valve 46. With further insertion, the flaps of valve 46 are forced open in an upstream direction allowing end 14a to pass inwardly through of valve 46. Collar 50 may then be tightened onto drainage conduit 12 completing the insertion of end 14a through valve 46. Waste material 8 from bowel 20 may then flow or readily pass through evacuation tube 14 and into waste receptacle 16 for disposal by the patient.

As will be apparent to those skilled in the art in the light of the foregoing disclosure, many alterations and modificaare possible in the practice of this invention without departing from the spirit or scope thereof. Accordingly, the scope of the invention is to be construed in accordance with the substance defined by the following claims.

What is claimed is:

1. A valved ostomy drainage device comprising:

hollow first and second conduits, said first conduit having first and second opposite ends, said first end having an inflatable annular anchor mounted thereto for selective inflation so as to anchor said first end with a patient's bowel ostomy behind the abdominal wall of the patient, and wherein said second end is cylindrical and externally threaded and said first conduit is of sufficient length so that, with said anchor inflated and snug against the interior surface of the abdominal wall, a portion of said second end protrudes from the stoma, wherein a threaded first collar is mountable onto said second end of said first conduit so that, once snugged adjacent the exterior surface of the abdomen, said inflated anchor is held snugly against the abdominal wall, and wherein, with said first collar so mounted, a length of said second end of said first conduit protrudes from said first collar, a sealing means mountable onto said second end of said first conduit to provide a removable and re-usable fluid and gas seal on said second end of said first conduit, and wherein a one-way valve is mounted in said first conduit.

2. The device of claim 1 wherein said sealing means is a cap.

3. The device of claim 1 wherein said second conduit slides in a telescoping fit into said first conduit and wherein said one-way valve is resiliently biased closed by biasing means to inhibit fluid flow from said first end to said second end of said first conduit.

4. The device of claim 3 wherein said one-way valve includes one-way opening means adapted to be pushed open by insertion of said second conduit in said sliding telescoping fit into said first conduit so as to journal a first end of said second conduit through said one-way opening means of said one-way valve and into fluid communication with said first end of said first conduit.

5. The device of claim 1 further comprising an attachment means mounted on said second conduit, so that, with said sealing means removed and said second conduit inserted into said first conduit and through said one-way valve, said attachment means is mountable onto said protruding portion of said second end protruding from said first collar.

6. The device of claim 5 wherein said attachment means is a threaded second collar threadably mountable onto said protruding portion of said second end.

7. The device of claim 6 wherein said second collar when mounted onto said protruding portion is adapted to seal, by second sealing means, said sliding telescoping fit of said second conduit into said first conduit when said second collar is snugly mated onto said second end of said first conduit.

8. The device of claim 1 further comprising a resilient pad adapted to be sandwiched between said first collar and the patient's abdomen.

9. A valved ostomy drainage device comprising a primary conduit for journalled mounting through an ostomy aperture in an abdomen, said primary conduit having an inner end for protrusion through the aperture, on the inner wall of abdomen, and an opposite outer end for protrusion outwardly of the aperture from the outer wall of the abdomen, an inflatable cuff mounted around said inner end of said primary conduit, said primary conduit having inflation means in fluid communication between said outer end and said cuff for inflation of said cuff when adjacent the inner wall of the abdomen, an anchoring collar releasably mountable onto said outer end of said primary conduit so as to sandwich the abdomen between said cuff, when inflated, and said anchoring collar, a releasably mountable end seal mountable onto said outer end for releasably sealing said outer end, a secondary conduit sized for mounting a first end thereof into and along said primary conduit, an opposite second end of said secondary conduit adapted for mounting of a waste container thereto, a one-way valve mounted in said primary conduit for preventing flow of waste in an outflow direction from said inner end to said outer end and for allowing said secondary conduit to be inserted through said one-way valve from said outer end of said primary conduit whereby waste then flows in said outflow direction through said secondary conduit.

10. The device of claim 9 further comprising a resilient pad seal mountable onto said outer end of said primary conduit so as to seal the aperture in the abdomen when said anchoring collar is mounted onto said outer end to thereby sandwich said ring seal between said anchoring collar and the abdomen.

11. The device of claim 9 wherein said outer end is threaded and wherein said end seal is a threaded cap for threaded mounting onto said outer end.

12. The device of claim 9 wherein said one-way valve is a flap valve mounted towards said outer end of said primary conduit.

13. The device of claim 9 wherein said inflation means is an air passageway having mounted therein a one-way check valve.

14. The device of claim 9 wherein said secondary conduit is L-shaped so that said second end is disposed downwardly when said first end is mounted through said one-way valve in said primary conduit.

15. The device of claim 14 wherein said waste container is a disposable ostomy bag.

16. The device of claim 13 wherein said inflation means further includes an air conduit mounted at one end in fluid communication with said passageway and an opposite end protruding outwardly of said pad seal and anchoring collar for releasable mating to an air pressurizing means.

* * * * *